US00PP26230P2

(12) United States Plant Patent
Ubink

(10) Patent No.: US PP26,230 P2
(45) Date of Patent: Dec. 15, 2015

(54) ***ECHEVERIA* PLANT NAMED 'HERCULES'**

(50) Latin Name: ***Echeveria pulidonis*×*E. elegans***
Varietal Denomination: Hercules

(71) Applicant: Gert Ubink, Kudelstaart (NL)

(72) Inventor: Gert Ubink, Kudelstaart (NL)

(73) Assignee: Handelskwekerij UBink B.V., Kudelstaart (NL)

( * ) Notice: Subject to any disclaimer, the term of this patent is extended or adjusted under 35 U.S.C. 154(b) by 134 days.

(21) Appl. No.: 13/998,627

(22) Filed: Nov. 18, 2013

(51) Int. Cl.
*A01H 5/00* (2006.01)

(52) U.S. Cl.
USPC ..... Plt./373

(58) Field of Classification Search
USPC ..... Plt./263.1, 373
See application file for complete search history.

*Primary Examiner* — Keith O. Robinson

(57) ABSTRACT

A new cultivar of *Echeveria* plant named 'Hercules' that is characterized by grey-green leaves with grey-purple margins and tips and a small overall size.

1 Drawing Sheet

Botanical classification: *Echeveria pulidonis*×*E. elegans*.
Variety denomination: 'Hercules'.

BACKGROUND OF THE INVENTION

The present invention relates to a new and distinct cultivar of *Echeveria* plant botanically known as *Echeveria pulidonis*×*E. elegans* and hereinafter referred to by the cultivar name 'Hercules'.

'Hercules' originated from the crossing of the female or seed parent, an unnamed proprietary *Echeveria pulidonis* cultivar, and the male or pollen parent, an unnamed proprietary *Echeveria elegans* cultivar. The crossing was conducted in 2006 in Kudelstaart, Netherlands. The resulting seeds were subsequently planted and grown. The cultivar 'Hercules' was selected by the inventor in 2008 in a controlled environment as a single plant within the progeny of the stated cross in a cultivated area of Kudelstaart, Netherlands.

Asexual reproduction of the new cultivar 'Hercules' first occurred by leaf cuttings in 2008 in Kudelstaart, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Echeveria* cultivar 'Hercules'. These traits in combination distinguish 'Hercules' as a new and distinct cultivar apart from other existing varieties of *Echeveria* known by the inventor.

1. *Echeveria* 'Hercules' exhibits grey-green leaves with grey-purple margins and tips.
2. *Echeveria* 'Hercules' exhibits a small overall size.

The closest comparison cultivar is the co-pending application cultivar *Echeveria* 'Orion' (U.S. Plant patent application Ser. No. 13/998,631). 'Hercules' is distinguishable from 'Orion' by the following characteristics:

1. *Echeveria* 'Hercules' exhibits leaves that have an upper side color that is grey-green. In comparison, the leaves of 'Orion' have an upper side color that is brown with a yellow-green base.
2. *Echeveria* 'Hercules' exhibits a leaf tip that is more red in color than the leaf tip of 'Orion'.
3. *Echeveria* 'Hercules' exhibits a smaller overall plant size than the plant size of 'Orion'.

'Hercules' is distinguishable from the female parent plant, an unnamed proprietary *Echeveria pulidonis* cultivar, by the following characteristics:

1. The leaves of 'Hercules' are shorter and narrower than the leaves of the female parent plant.
2. The leaves of 'Hercules' have leaf tips that are more rounded than the leaf tips of the female parent plant.

'Hercules' is distinguishable from the male parent plant, an unnamed proprietary *Echeveria elegans* cultivar, by the following characteristics:

1. The leaves of 'Hercules' are grey-green in color. The leaves of the male parent plant are blue-green in color.
2. The leaves of 'Hercules' have grey-purple colored margins that are more red than the margins of the male parent plant.
3. The leaves of 'Hercules' have wider margins than the margins of the male parent plant.

BRIEF DESCRIPTION OF THE DRAWING

The accompanying photographs illustrate the distinguishing traits of *Echeveria* 'Hercules'.

Figure 1:
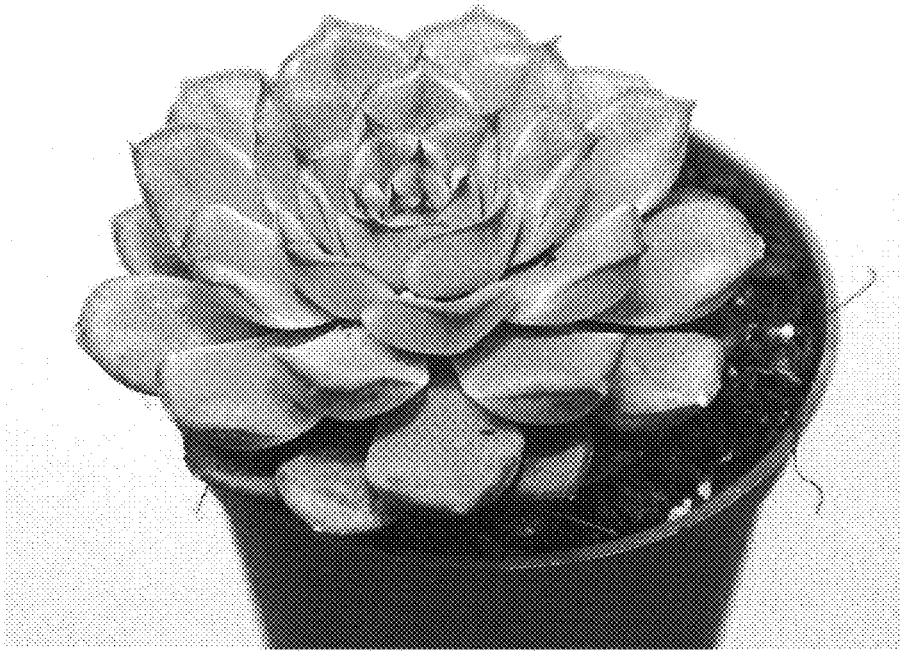
FIG. 1 shows an overall view of a 14 month old plant.
Figure 2:
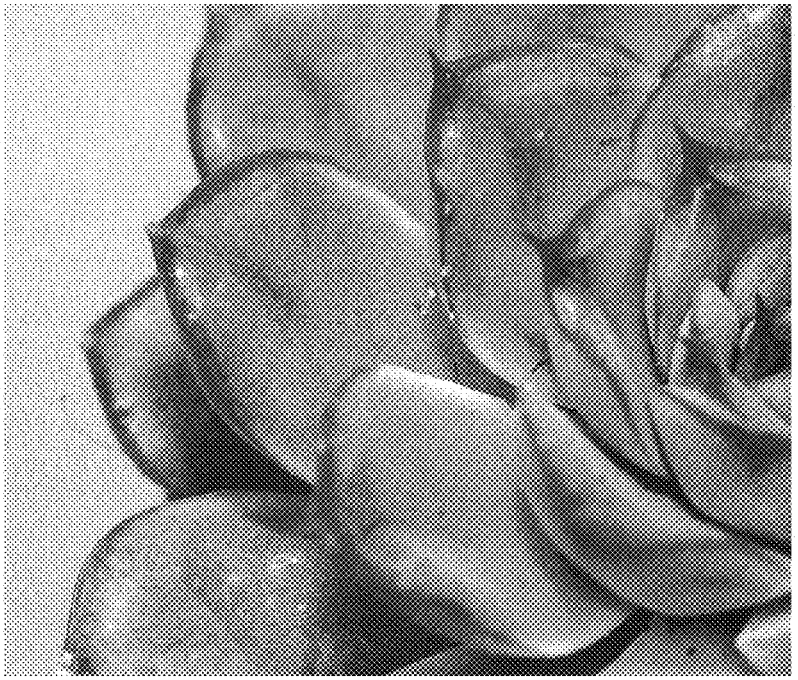
FIG. 2 shows an enlarged view of the leaves.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Echeveria* cultivar named 'Hercules'. Data was collected in Kudelstaart, Netherlands from 14 month old plants grown in a glass greenhouse in 10.5 cm. diameter containers. The time of year was Autumn and the temperature range was 18-25 degrees Centigrade during the day and 12-18 degrees Centigrade at night. The light level was natural light level. No photoperiodic treatments or growth retards were used. Color determinations are in accordance with The Royal Horticultural Society Colour Chart 2007 edition, except where general color terms of ordinary dictionary significance are used. The growing requirements are similar to the species. 'Hercules' has not been tested under all possible conditions and phenotypic differences may be observed with variations in environmental, climatic, and cultural conditions, however, without any variance in genotype.

Botanical classification: *Echeveria pulidonis*×*E. elegans* 'Hercules'.

Annual or perennial: Perennial.

Parentage: 'Hercules' is a hybrid of the female parent an unnamed proprietary *Echeveria pulidonis* cultivar and the male parent an unnamed proprietary *Echeveria elegans* cultivar.

Plant type: Pot plant.

Plant shape: Basal rosette.

Suitable container size: 8.5 cm. pots or larger.

Plant height: 4.2 cm.

Plant width: 8.5 cm.

Vigor: Moderate.

Low temperature tolerance: 10° Centigrade.

High temperature tolerance: 40° Centigrade.

Propagation: Leaf cuttings.

Time to initiate roots (summer): 14 days at 20° C.

Time to initiate roots (winter): 21 days at 20° C.

Time to produce a rooted cutting (summer): 120 days at 20° C.

Time to produce a rooted cutting (winter): 150 days at 20° C.

Growth rate: Approximately 0.2 cm. per month.

Crop time: Approximately 5 months from July to November in Kudelstaart, Netherlands.

Root system: Fibrous.

Root color: N155.

Plant fragrance: None.

Foliage:

*Leaf arrangement*.—Basal rosette.

*Compound or single*.—Single.

*Quantity of leaves per plant*.—Average 70.

*Leaf shape*.—Oblanceolate, slightly carinate.

*Leaf apex*.—Acute.

*Leaf base*.—Broad cuneate.

*Leaf dimensions*.—2.9 cm. in length and 1.9 cm. in width.

*Leaf thickness*.—0.6 cm.

*Texture*.—Glabrous both surfaces, succulent.

*Pubescence*.—Absent.

*Leaf margin*.—Entire.

*Venation pattern*.—None visible.

*Young leaf color* (*upper surface*).—189A, base 136C, margins and tip 183C, upper surface covered by waxy layer 188A.

*Young leaf color* (*lower surface*).—191A, margins and tip 183D, lower surface covered by waxy layer 188B.

*Mature leaf color* (*upper surface*).—Between 189A and 191A, margins and tip 183C, upper surface covered by waxy layer 188B.

*Mature leaf color* (*lower surface*).—Between 148B and 191B, margins and tip 184C, lower surface covered by waxy layer 188B.

*Leaf attachment*.—Sessile.

Flower: No flowers have been observed to date.

Fruit and seed: No fruit or seed production has been observed to date.

Disease and pest resistance: Disease and pest resistance has not been observed.

The invention claimed is:

1. A new and distinct variety of *Echeveria* plant named 'Hercules' as described and illustrated.

* * * * *